(12) United States Patent
Govari et al.

(10) Patent No.: US 12,364,426 B2
(45) Date of Patent: Jul. 22, 2025

(54) ELECTRO-ANATOMICAL MAPPING AND ANNOTATION PRESENTED IN ELECTROPHYSIOLOGICAL PROCEDURES

(71) Applicant: BIOSENSE WEBSTER (ISRAEL) LTD., Yokneam (IL)

(72) Inventors: Assaf Govari, Haifa (IL); Andres Claudio Altmann, Haifa (IL); Vadim Gliner, Haifa (IL)

(73) Assignee: Biosense Webster (Israel) Ltd., Yokneam (IL)

( * ) Notice: Subject to any disclaimer, the term of this patent is extended or adjusted under 35 U.S.C. 154(b) by 442 days.

(21) Appl. No.: 17/400,402

(22) Filed: Aug. 12, 2021

(65) Prior Publication Data
US 2023/0052130 A1 Feb. 16, 2023

(51) Int. Cl.
*A61B 5/287* (2021.01)
*A61B 5/367* (2021.01)

(52) U.S. Cl.
CPC .............. *A61B 5/287* (2021.01); *A61B 5/367* (2021.01)

(58) Field of Classification Search
CPC ................................. A61B 5/387; A61B 5/367
USPC ........................................................ 600/509
See application file for complete search history.

(56) References Cited

U.S. PATENT DOCUMENTS

| | | | |
|---|---|---|---|
| 4,699,147 A | 10/1987 | Chilson et al. | |
| 4,940,064 A | 7/1990 | Desai | |
| 5,215,103 A | 6/1993 | Desai | |
| 5,255,679 A | 10/1993 | Imran | |
| 5,293,869 A | 3/1994 | Edwards et al. | |
| 5,309,910 A | 5/1994 | Edwards et al. | |
| 5,313,943 A | 5/1994 | Houser et al. | |
| 5,324,284 A | 6/1994 | Imran | |
| 5,345,936 A | 9/1994 | Pomeranz et al. | |
| 5,365,926 A | 11/1994 | Desai | |
| 5,391,199 A | 2/1995 | Ben-Haim | |
| 5,396,887 A | 3/1995 | Imran | |

(Continued)

FOREIGN PATENT DOCUMENTS

| CN | 110051346 A | * 7/2019 | ........... A61B 5/0422 |
|---|---|---|---|
| CN | 111248993 A | 6/2020 | |

(Continued)

OTHER PUBLICATIONS

Extended European Search Report dated Jan. 20, 2023, from corresponding European Application No. 22189869.5.

*Primary Examiner* — Nicole F Johnson (57) ABSTRACT

A catheter includes: (a) a shaft for insertion into a heart of a patient, (b) an expandable distal-end assembly, which is coupled to the shaft and is configured to make contact with tissue of the heart, (c) at least first and second electrocardiogram (ECG) electrodes, which are coupled to an outer surface of the expandable distal-end assembly, and when placed in contact with the tissue, are configured to sense ECG signals in the tissue, and (d) a reference electrode, which is positioned within an inner volume of the distal-end assembly, and in an expanded position of the distal-end assembly, the reference electrode: (i) has no physical contact with the tissue, and (ii) is positioned at a first distance from the first ECG electrode and at a second distance from the second ECG electrode, and the difference between the first and second distances is smaller than a predefined threshold.

14 Claims, 3 Drawing Sheets

(56) References Cited

U.S. PATENT DOCUMENTS

| | | |
|---|---|---|
| 5,400,783 A | 3/1995 | Pomeranz et al. |
| 5,411,025 A | 5/1995 | Webster, Jr. |
| 5,415,166 A | 5/1995 | Imran |
| 5,456,254 A | 10/1995 | Pietroski et al. |
| 5,465,717 A | 11/1995 | Imran et al. |
| 5,476,495 A | 12/1995 | Kordis et al. |
| 5,499,981 A | 3/1996 | Kordis |
| 5,526,810 A | 6/1996 | Wang |
| 5,546,940 A | 8/1996 | Panescu et al. |
| 5,549,108 A | 8/1996 | Edwards et al. |
| 5,558,073 A | 9/1996 | Pomeranz et al. |
| 5,577,509 A | 11/1996 | Panescu et al. |
| 5,595,183 A | 1/1997 | Swanson et al. |
| 5,598,848 A | 2/1997 | Swanson et al. |
| 5,609,157 A | 3/1997 | Panescu et al. |
| 5,628,313 A | 5/1997 | Webster, Jr. |
| 5,681,280 A | 10/1997 | Rusk et al. |
| 5,722,401 A | 3/1998 | Pietroski et al. |
| 5,722,403 A | 3/1998 | McGee et al. |
| 5,725,525 A | 3/1998 | Kordis |
| 5,730,128 A | 3/1998 | Pomeranz et al. |
| 5,772,590 A | 6/1998 | Webster, Jr. |
| 5,782,899 A | 7/1998 | Imran |
| 5,823,189 A | 10/1998 | Kordis |
| 5,881,727 A | 3/1999 | Edwards |
| 5,893,847 A | 4/1999 | Kordis |
| 5,904,680 A | 5/1999 | Kordis et al. |
| 5,911,739 A | 6/1999 | Kordis et al. |
| 5,928,228 A | 7/1999 | Kordis et al. |
| 5,968,040 A | 10/1999 | Swanson et al. |
| 6,014,579 A | 1/2000 | Pomeranz et al. |
| 6,014,590 A | 1/2000 | Whayne et al. |
| 6,119,030 A | 9/2000 | Morency |
| 6,216,043 B1 | 4/2001 | Swanson et al. |
| 6,216,044 B1 | 4/2001 | Kordis |
| 6,239,724 B1 | 5/2001 | Doron et al. |
| 6,332,089 B1 | 12/2001 | Acker et al. |
| 6,428,537 B1 | 8/2002 | Swanson et al. |
| 6,456,864 B1 | 9/2002 | Swanson et al. |
| 6,484,118 B1 | 11/2002 | Govari |
| 6,574,492 B1 | 6/2003 | Ben-Haim et al. |
| 6,584,345 B2 | 6/2003 | Govari |
| 6,600,948 B2 | 7/2003 | Ben-Haim et al. |
| 6,618,612 B1 | 9/2003 | Acker et al. |
| 6,690,963 B2 | 2/2004 | Ben-Haim et al. |
| 6,738,655 B1 | 5/2004 | Sen et al. |
| 6,741,878 B2 | 5/2004 | Fuimaono et al. |
| 6,748,255 B2 | 6/2004 | Fuimaono et al. |
| 6,780,183 B2 | 8/2004 | Jimenez, Jr. et al. |
| 6,837,886 B2 | 1/2005 | Collins et al. |
| 6,866,662 B2 | 3/2005 | Fuimaono et al. |
| 6,892,091 B1 | 5/2005 | Ben-Haim et al. |
| 6,970,730 B2 | 11/2005 | Fuimaono et al. |
| 6,973,340 B2 | 12/2005 | Fuimaono et al. |
| 6,980,858 B2 | 12/2005 | Fuimaono et al. |
| 7,048,734 B1 | 5/2006 | Fleischman et al. |
| 7,149,563 B2 | 12/2006 | Fuimaono et al. |
| 7,255,695 B2 | 8/2007 | Falwell et al. |
| 7,257,434 B2 | 8/2007 | Fuimaono et al. |
| 7,399,299 B2 | 7/2008 | Daniel et al. |
| 7,410,486 B2 | 8/2008 | Fuimaono et al. |
| 7,522,950 B2 | 4/2009 | Fuimaono et al. |
| RE41,334 E | 5/2010 | Beatty et al. |
| 7,846,157 B2 | 12/2010 | Kozel |
| 7,930,018 B2 | 4/2011 | Harlev et al. |
| 8,007,495 B2 | 8/2011 | McDaniel et al. |
| 8,048,063 B2 | 11/2011 | Aeby et al. |
| 8,103,327 B2 | 1/2012 | Harlev et al. |
| 8,167,845 B2 | 5/2012 | Wang et al. |
| 8,224,416 B2 | 7/2012 | De La Rama et al. |
| 8,235,988 B2 | 8/2012 | Davis et al. |
| 8,346,339 B2 | 1/2013 | Kordis et al. |
| 8,435,232 B2 | 5/2013 | Aeby et al. |
| 8,447,377 B2 | 5/2013 | Harlev et al. |
| 8,498,686 B2 | 7/2013 | Grunewald |
| 8,517,999 B2 | 8/2013 | Pappone et al. |
| 8,545,490 B2 | 10/2013 | Mihajlovic et al. |
| 8,560,086 B2 | 10/2013 | Just et al. |
| 8,567,265 B2 | 10/2013 | Aeby et al. |
| 8,712,550 B2 | 4/2014 | Grunewald |
| 8,755,861 B2 | 6/2014 | Harlev et al. |
| 8,825,130 B2 | 9/2014 | Just et al. |
| 8,906,011 B2 | 12/2014 | Gelbart et al. |
| 8,945,120 B2 | 2/2015 | McDaniel et al. |
| 8,979,839 B2 | 3/2015 | De La Rama et al. |
| 9,037,264 B2 | 5/2015 | Just et al. |
| 9,131,980 B2 | 9/2015 | Bloom |
| 9,204,929 B2 | 12/2015 | Solis |
| 9,277,960 B2 | 3/2016 | Weinkam et al. |
| 9,314,208 B1 | 4/2016 | Altmann et al. |
| 9,339,331 B2 | 5/2016 | Tegg et al. |
| 9,486,282 B2 | 11/2016 | Solis |
| 9,554,718 B2 | 1/2017 | Bar-Tal et al. |
| D782,686 S | 3/2017 | Werneth et al. |
| 9,585,588 B2 | 3/2017 | Marecki et al. |
| 9,597,036 B2 | 3/2017 | Aeby et al. |
| 9,687,297 B2 | 6/2017 | Just et al. |
| 9,693,733 B2 | 7/2017 | Altmann et al. |
| 9,782,099 B2 | 10/2017 | Williams et al. |
| 9,788,895 B2 | 10/2017 | Solis |
| 9,801,681 B2 | 10/2017 | Laske et al. |
| 9,814,618 B2 | 11/2017 | Nguyen et al. |
| 9,833,161 B2 | 12/2017 | Govari |
| 9,894,756 B2 | 2/2018 | Weinkam et al. |
| 9,895,073 B2 | 2/2018 | Solis |
| 9,907,609 B2 | 3/2018 | Cao et al. |
| 9,974,460 B2 | 5/2018 | Wu et al. |
| 9,986,949 B2 | 6/2018 | Govari et al. |
| 9,993,160 B2 | 6/2018 | Salvestro et al. |
| 10,014,607 B1 | 7/2018 | Govari et al. |
| 10,028,376 B2 | 7/2018 | Weinkam et al. |
| 10,034,637 B2 | 7/2018 | Harlev et al. |
| 10,039,494 B2 | 8/2018 | Altmann et al. |
| 10,045,707 B2 | 8/2018 | Govari |
| 10,078,713 B2 | 9/2018 | Auerbach et al. |
| 10,111,623 B2 | 10/2018 | Jung et al. |
| 10,130,420 B2 | 11/2018 | Basu et al. |
| 10,136,828 B2 | 11/2018 | Houben et al. |
| 10,143,394 B2 | 12/2018 | Solis |
| 10,172,536 B2 | 1/2019 | Maskara et al. |
| 10,182,762 B2 | 1/2019 | Just et al. |
| 10,194,818 B2 | 2/2019 | Williams et al. |
| 10,201,311 B2 | 2/2019 | Chou et al. |
| 10,219,860 B2 | 3/2019 | Harlev et al. |
| 10,219,861 B2 | 3/2019 | Just et al. |
| 10,231,328 B2 | 3/2019 | Weinkam et al. |
| 10,238,309 B2 | 3/2019 | Bar-Tal et al. |
| 10,278,590 B2 | 5/2019 | Salvestro et al. |
| D851,774 S | 6/2019 | Werneth et al. |
| 10,314,505 B2 | 6/2019 | Williams et al. |
| 10,314,507 B2 | 6/2019 | Govari et al. |
| 10,314,648 B2 | 6/2019 | Ge et al. |
| 10,314,649 B2 | 6/2019 | Bakos et al. |
| 10,349,855 B2 | 7/2019 | Zeidan et al. |
| 10,350,003 B2 | 7/2019 | Weinkam et al. |
| 10,362,991 B2 | 7/2019 | Tran et al. |
| 10,375,827 B2 | 8/2019 | Weinkam et al. |
| 10,376,170 B2 | 8/2019 | Quinn et al. |
| 10,376,221 B2 | 8/2019 | Iyun et al. |
| 10,398,348 B2 | 9/2019 | Osadchy et al. |
| 10,403,053 B2 | 9/2019 | Katz et al. |
| 10,441,188 B2 | 10/2019 | Katz et al. |
| 10,470,682 B2 | 11/2019 | Deno et al. |
| 10,470,714 B2 | 11/2019 | Altmann et al. |
| 10,482,198 B2 | 11/2019 | Auerbach et al. |
| 10,492,857 B2 | 12/2019 | Guggenberger et al. |
| 10,542,620 B2 | 1/2020 | Weinkam et al. |
| 10,575,743 B2 | 3/2020 | Basu et al. |
| 10,575,745 B2 | 3/2020 | Solis |
| 10,582,871 B2 | 3/2020 | Williams et al. |
| 10,582,894 B2 | 3/2020 | Ben Zrihem et al. |
| 10,596,346 B2 | 3/2020 | Aeby et al. |
| 10,602,947 B2 | 3/2020 | Govari et al. |
| 10,617,867 B2 | 4/2020 | Viswanathan et al. |

(56) References Cited

U.S. PATENT DOCUMENTS

| | | |
|---|---|---|
| 10,660,702 B2 | 5/2020 | Viswanathan et al. |
| 10,667,753 B2 | 6/2020 | Werneth et al. |
| 10,674,929 B2 | 6/2020 | Houben et al. |
| 10,681,805 B2 | 6/2020 | Weinkam et al. |
| 10,682,181 B2 | 6/2020 | Cohen et al. |
| 10,687,892 B2 | 6/2020 | Long et al. |
| 10,702,178 B2 | 7/2020 | Dahlen et al. |
| 10,716,477 B2 | 7/2020 | Salvestro et al. |
| 10,758,304 B2 | 9/2020 | Aujla |
| 10,765,371 B2 | 9/2020 | Hayam et al. |
| 10,772,566 B2 | 9/2020 | Aujila |
| 10,799,281 B2 | 10/2020 | Goertzen et al. |
| 10,842,558 B2 | 11/2020 | Harlev et al. |
| 10,842,561 B2 | 11/2020 | Mswanathan et al. |
| 10,863,914 B2 | 12/2020 | Govari et al. |
| 10,881,376 B2 | 1/2021 | Shemesh et al. |
| 10,898,139 B2 | 1/2021 | Guta et al. |
| 10,905,329 B2 | 2/2021 | Bar-Tal et al. |
| 10,912,484 B2 | 2/2021 | Ziv-Ari et al. |
| 10,918,306 B2 | 2/2021 | Govari et al. |
| 10,939,871 B2 | 3/2021 | Altmann et al. |
| 10,952,795 B2 | 3/2021 | Cohen et al. |
| 10,973,426 B2 | 4/2021 | Williams et al. |
| 10,973,461 B2 | 4/2021 | Baram et al. |
| 10,987,045 B2 | 4/2021 | Basu et al. |
| 11,006,902 B1 | 5/2021 | Bonyak et al. |
| 11,040,208 B1 | 6/2021 | Govari et al. |
| 11,045,628 B2 | 6/2021 | Beeckler et al. |
| 11,051,877 B2 | 7/2021 | Sliwa et al. |
| 11,109,788 B2 | 9/2021 | Rottmann et al. |
| 11,116,435 B2 | 9/2021 | Urman et al. |
| 11,129,574 B2 | 9/2021 | Cohen et al. |
| 11,160,482 B2 | 11/2021 | Solis |
| 11,164,371 B2 | 11/2021 | Yellin et al. |
| 2002/0065455 A1 | 5/2002 | Ben-Haim et al. |
| 2003/0120150 A1 | 6/2003 | Govari |
| 2004/0068178 A1 | 4/2004 | Govari |
| 2004/0210121 A1 | 10/2004 | Fuimaono et al. |
| 2006/0009689 A1 | 1/2006 | Fuimaono et al. |
| 2006/0009690 A1 | 1/2006 | Fuimaono et al. |
| 2006/0100669 A1 | 5/2006 | Fuimaono et al. |
| 2007/0093806 A1 | 4/2007 | Desai et al. |
| 2007/0276212 A1 | 11/2007 | Fuimaono et al. |
| 2008/0234564 A1 | 9/2008 | Beatty et al. |
| 2011/0028820 A1 | 2/2011 | Lau et al. |
| 2011/0118726 A1 | 5/2011 | De La Rama et al. |
| 2011/0160574 A1 | 6/2011 | Harlev et al. |
| 2011/0190625 A1 | 8/2011 | Harlev et al. |
| 2011/0245756 A1 | 10/2011 | Arora et al. |
| 2011/0301597 A1 | 12/2011 | McDaniel et al. |
| 2013/0172872 A1 | 7/2013 | Subramaniam et al. |
| 2013/0172883 A1 | 7/2013 | Lopes et al. |
| 2013/0178850 A1 | 7/2013 | Lopes et al. |
| 2013/0190587 A1 | 7/2013 | Lopes et al. |
| 2013/0296852 A1 | 11/2013 | Madjarov et al. |
| 2014/0025069 A1 | 1/2014 | Willard et al. |
| 2014/0052118 A1 | 2/2014 | Laske et al. |
| 2014/0180147 A1 | 6/2014 | Thakur et al. |
| 2014/0180151 A1 | 6/2014 | Maskara et al. |
| 2014/0180152 A1 | 6/2014 | Maskara et al. |
| 2014/0257069 A1 | 9/2014 | Eliason et al. |
| 2014/0276712 A1 | 9/2014 | Mallin et al. |
| 2014/0309512 A1 | 10/2014 | Govari et al. |
| 2015/0011991 A1 | 1/2015 | Buysman et al. |
| 2015/0045863 A1 | 2/2015 | Litscher et al. |
| 2015/0080693 A1 | 3/2015 | Solis |
| 2015/0105770 A1 | 4/2015 | Amit |
| 2015/0119878 A1 | 4/2015 | Heisel et al. |
| 2015/0133919 A1 | 5/2015 | McDaniel et al. |
| 2015/0208942 A1 | 7/2015 | Bar-Tal et al. |
| 2015/0250424 A1 | 9/2015 | Govari et al. |
| 2015/0270634 A1 | 9/2015 | Buesseler et al. |
| 2015/0342532 A1 | 12/2015 | Basu et al. |
| 2016/0081746 A1 | 3/2016 | Solis |
| 2016/0113582 A1 | 4/2016 | Altmann et al. |
| 2016/0113709 A1 | 4/2016 | Maor |
| 2016/0183877 A1 | 6/2016 | Williams et al. |
| 2016/0228023 A1 | 8/2016 | Govari |
| 2016/0228062 A1 | 8/2016 | Altmann et al. |
| 2016/0278853 A1 | 9/2016 | Ogle et al. |
| 2016/0302858 A1 | 10/2016 | Bencini |
| 2016/0338770 A1 | 11/2016 | Bar-Tal et al. |
| 2017/0027638 A1 | 2/2017 | Solis |
| 2017/0065227 A1 | 3/2017 | Marrs et al. |
| 2017/0071543 A1 | 3/2017 | Basu et al. |
| 2017/0071544 A1 | 3/2017 | Basu et al. |
| 2017/0071665 A1 | 3/2017 | Solis |
| 2017/0095173 A1 | 4/2017 | Bar-Tal et al. |
| 2017/0100187 A1 | 4/2017 | Basu et al. |
| 2017/0143227 A1 | 5/2017 | Marecki et al. |
| 2017/0156790 A1 | 6/2017 | Aujla |
| 2017/0172442 A1 | 6/2017 | Govari |
| 2017/0185702 A1 | 6/2017 | Auerbach et al. |
| 2017/0202515 A1 | 7/2017 | Zrihem et al. |
| 2017/0221262 A1 | 8/2017 | Laughner et al. |
| 2017/0224958 A1 | 8/2017 | Cummings et al. |
| 2017/0265812 A1 | 9/2017 | Williams et al. |
| 2017/0281031 A1 | 10/2017 | Houben et al. |
| 2017/0281268 A1 | 10/2017 | Tran et al. |
| 2017/0296084 A1 | 10/2017 | Blauer et al. |
| 2017/0296125 A1 | 10/2017 | Altmann et al. |
| 2017/0296251 A1 | 10/2017 | Wu et al. |
| 2017/0347959 A1 | 12/2017 | Guta et al. |
| 2017/0354338 A1 | 12/2017 | Levin et al. |
| 2017/0354339 A1 | 12/2017 | Zeidan et al. |
| 2017/0354364 A1 | 12/2017 | Bar-Tal et al. |
| 2018/0008203 A1 | 1/2018 | Iyun et al. |
| 2018/0028084 A1 | 2/2018 | Williams et al. |
| 2018/0049803 A1 | 2/2018 | Solis |
| 2018/0085064 A1 | 3/2018 | Auerbach et al. |
| 2018/0132749 A1 | 5/2018 | Govari et al. |
| 2018/0137687 A1 | 5/2018 | Katz et al. |
| 2018/0160936 A1 | 6/2018 | Govari et al. |
| 2018/0160978 A1 | 6/2018 | Cohen et al. |
| 2018/0168511 A1 | 6/2018 | Hall et al. |
| 2018/0184982 A1 | 7/2018 | Basu et al. |
| 2018/0192958 A1 | 7/2018 | Wu |
| 2018/0206792 A1 | 7/2018 | Auerbach et al. |
| 2018/0235692 A1 | 8/2018 | Efimov et al. |
| 2018/0249959 A1 | 9/2018 | Osypka |
| 2018/0256109 A1 | 9/2018 | Wu et al. |
| 2018/0279954 A1 | 10/2018 | Hayam et al. |
| 2018/0303414 A1 | 10/2018 | Toth et al. |
| 2018/0310987 A1 | 11/2018 | Altmann et al. |
| 2018/0311497 A1 | 11/2018 | Viswanathan et al. |
| 2018/0338722 A1 | 11/2018 | Altmann et al. |
| 2018/0344188 A1 | 12/2018 | Govari |
| 2018/0344202 A1 | 12/2018 | Bar-Tal et al. |
| 2018/0344251 A1 | 12/2018 | Harlev et al. |
| 2018/0344393 A1 | 12/2018 | Gruba et al. |
| 2018/0360534 A1 | 12/2018 | Teplitsky et al. |
| 2018/0365355 A1 | 12/2018 | Auerbach et al. |
| 2019/0000540 A1 | 1/2019 | Cohen et al. |
| 2019/0008582 A1 | 1/2019 | Govari et al. |
| 2019/0015007 A1 | 1/2019 | Rottmann et al. |
| 2019/0030328 A1 | 1/2019 | Stewart et al. |
| 2019/0053708 A1 | 2/2019 | Gliner |
| 2019/0059766 A1 | 2/2019 | Houben et al. |
| 2019/0069950 A1 | 3/2019 | Viswanathan et al. |
| 2019/0069954 A1 | 3/2019 | Cohen et al. |
| 2019/0117111 A1 | 4/2019 | Osadchy et al. |
| 2019/0117303 A1 | 4/2019 | Claude et al. |
| 2019/0117315 A1 | 4/2019 | Keyes et al. |
| 2019/0125439 A1 | 5/2019 | Rohl et al. |
| 2019/0133552 A1 | 5/2019 | Shemesh et al. |
| 2019/0142293 A1 | 5/2019 | Solis |
| 2019/0164633 A1 | 5/2019 | Ingel et al. |
| 2019/0167137 A1 | 6/2019 | Bar-Tal et al. |
| 2019/0167140 A1 | 6/2019 | Williams et al. |
| 2019/0188909 A1 | 6/2019 | Yellin et al. |
| 2019/0201664 A1 | 7/2019 | Govari |
| 2019/0209089 A1 | 7/2019 | Baram et al. |
| 2019/0216346 A1 | 7/2019 | Ghodrati et al. |
| 2019/0216347 A1 | 7/2019 | Ghodrati et al. |

(56) References Cited

U.S. PATENT DOCUMENTS

| | | |
|---|---|---|
| 2019/0231421 A1 | 8/2019 | Viswanathan et al. |
| 2019/0231423 A1 | 8/2019 | Weinkam et al. |
| 2019/0239811 A1 | 8/2019 | Just et al. |
| 2019/0246935 A1 | 8/2019 | Govari et al. |
| 2019/0298442 A1 | 10/2019 | Ogata et al. |
| 2019/0314083 A1 | 10/2019 | Herrera et al. |
| 2019/0328258 A1* | 10/2019 | Gaeta ................ A61B 5/282 |
| 2019/0328260 A1 | 10/2019 | Zeidan et al. |
| 2019/0343580 A1 | 11/2019 | Nguyen et al. |
| 2020/0000518 A1 | 1/2020 | Kiernan et al. |
| 2020/0008705 A1 | 1/2020 | Ziv-Ari et al. |
| 2020/0008869 A1 | 1/2020 | Byrd |
| 2020/0009378 A1 | 1/2020 | Stewart et al. |
| 2020/0015890 A1 | 1/2020 | To et al. |
| 2020/0022653 A1 | 1/2020 | Moisa |
| 2020/0029845 A1 | 1/2020 | Baram et al. |
| 2020/0046421 A1 | 2/2020 | Govari |
| 2020/0046423 A1 | 2/2020 | Viswanathan et al. |
| 2020/0060569 A1 | 2/2020 | Tegg |
| 2020/0077959 A1 | 3/2020 | Altmann et al. |
| 2020/0093539 A1 | 3/2020 | Long et al. |
| 2020/0129089 A1 | 4/2020 | Gliner et al. |
| 2020/0129125 A1 | 4/2020 | Govari et al. |
| 2020/0129128 A1 | 4/2020 | Gliner et al. |
| 2020/0179650 A1 | 6/2020 | Beeckler et al. |
| 2020/0196896 A1 | 6/2020 | Solis |
| 2020/0205689 A1 | 7/2020 | Squires et al. |
| 2020/0205690 A1 | 7/2020 | Williams et al. |
| 2020/0205737 A1 | 7/2020 | Beeckler |
| 2020/0205876 A1 | 7/2020 | Govari |
| 2020/0205892 A1 | 7/2020 | Mswanathan et al. |
| 2020/0206461 A1 | 7/2020 | Govari et al. |
| 2020/0206498 A1 | 7/2020 | Arora et al. |
| 2020/0289197 A1 | 9/2020 | Viswanathan et al. |
| 2020/0297234 A1 | 9/2020 | Houben et al. |
| 2020/0297281 A1 | 9/2020 | Basu et al. |
| 2020/0305726 A1 | 10/2020 | Salvestro et al. |
| 2020/0305946 A1 | 10/2020 | DeSimone et al. |
| 2020/0367751 A1 | 11/2020 | Vandersickel et al. |
| 2020/0397328 A1 | 12/2020 | Altmann et al. |
| 2020/0398048 A1 | 12/2020 | Krimsky et al. |
| 2021/0015549 A1 | 1/2021 | Haghighi-Mood et al. |
| 2021/0022684 A1 | 1/2021 | Govari et al. |
| 2021/0045805 A1 | 2/2021 | Govari et al. |
| 2021/0059549 A1 | 3/2021 | Urman et al. |
| 2021/0059550 A1 | 3/2021 | Urman et al. |
| 2021/0059608 A1 | 3/2021 | Beeckler et al. |
| 2021/0059743 A1 | 3/2021 | Govari |
| 2021/0059747 A1 | 3/2021 | Krans et al. |
| 2021/0077184 A1 | 3/2021 | Basu et al. |
| 2021/0082157 A1 | 3/2021 | Rosenberg et al. |
| 2021/0085200 A1 | 3/2021 | Auerbach et al. |
| 2021/0085204 A1 | 3/2021 | Auerbach et al. |
| 2021/0085215 A1 | 3/2021 | Auerbach et al. |
| 2021/0085387 A1 | 3/2021 | Amit et al. |
| 2021/0093292 A1 | 4/2021 | Baram et al. |
| 2021/0093294 A1 | 4/2021 | Shemesh et al. |
| 2021/0093374 A1 | 4/2021 | Govari et al. |
| 2021/0093377 A1 | 4/2021 | Herrera et al. |
| 2021/0100612 A1 | 4/2021 | Baron et al. |
| 2021/0113822 A1 | 4/2021 | Beeckler et al. |
| 2021/0127999 A1 | 5/2021 | Govari et al. |
| 2021/0128010 A1 | 5/2021 | Govari et al. |
| 2021/0133516 A1 | 5/2021 | Govari et al. |
| 2021/0145282 A1 | 5/2021 | Bar-Tal et al. |
| 2021/0169421 A1 | 6/2021 | Govari |
| 2021/0169568 A1 | 6/2021 | Govari et al. |
| 2021/0177294 A1 | 6/2021 | Gliner et al. |
| 2021/0177356 A1 | 6/2021 | Gliner et al. |
| 2021/0178166 A1 | 6/2021 | Govari et al. |
| 2021/0186363 A1 | 6/2021 | Gliner et al. |
| 2021/0187241 A1 | 6/2021 | Govari et al. |
| 2021/0196372 A1 | 7/2021 | Altmann et al. |
| 2021/0196394 A1 | 7/2021 | Govari et al. |
| 2021/0212591 A1 | 7/2021 | Govari et al. |
| 2021/0219904 A1 | 7/2021 | Yarnitsky et al. |
| 2021/0278936 A1 | 9/2021 | Katz et al. |
| 2021/0282659 A1 | 9/2021 | Govari et al. |
| 2021/0307815 A1 | 10/2021 | Govari et al. |
| 2021/0308424 A1 | 10/2021 | Beeckler et al. |
| 2021/0338319 A1 | 11/2021 | Govari et al. |

FOREIGN PATENT DOCUMENTS

| | | | |
|---|---|---|---|
| CN | 111248996 A | 6/2020 | |
| EP | 0668740 A1 | 8/1995 | |
| EP | 0644738 B1 | 3/2000 | |
| EP | 0727183 B1 | 11/2002 | |
| EP | 0727184 B1 | 12/2002 | |
| EP | 2783651 A1 | 10/2014 | |
| EP | 2699151 B1 | 11/2015 | |
| EP | 2699152 B1 | 11/2015 | |
| EP | 2699153 B1 | 12/2015 | |
| EP | 2498706 B1 | 4/2016 | |
| EP | 3053517 A1 * | 8/2016 | ............ A61B 18/12 |
| EP | 2578173 B1 | 6/2017 | |
| EP | 3238645 A1 | 11/2017 | |
| EP | 2884931 B1 | 1/2018 | |
| EP | 2349440 B1 | 8/2019 | |
| EP | 3318211 B1 | 12/2019 | |
| EP | 3581135 A1 | 12/2019 | |
| EP | 2736434 B1 | 2/2020 | |
| EP | 3451962 B1 | 3/2020 | |
| EP | 3972510 A1 | 3/2022 | |
| WO | 9421167 A1 | 9/1994 | |
| WO | 9421169 A1 | 9/1994 | |
| WO | WO9605768 | 2/1996 | |
| WO | 9625095 A1 | 8/1996 | |
| WO | 9634560 A1 | 11/1996 | |
| WO | 0182814 B1 | 5/2002 | |
| WO | 2004087249 A2 | 10/2004 | |
| WO | 2012100185 A2 | 7/2012 | |
| WO | 2013052852 A1 | 4/2013 | |
| WO | 2013162884 A1 | 10/2013 | |
| WO | 2013173917 A1 | 11/2013 | |
| WO | 2013176881 A1 | 11/2013 | |
| WO | 2014176205 A1 | 10/2014 | |
| WO | 2016019760 A1 | 2/2016 | |
| WO | 2016044687 A1 | 3/2016 | |
| WO | 2018111600 A1 | 6/2018 | |
| WO | 2018191149 A1 | 10/2018 | |
| WO | 2019084442 A1 | 5/2019 | |
| WO | 2019143960 A1 | 7/2019 | |
| WO | WO-2019144103 A1 * | 7/2019 | ......... A61B 18/1492 |
| WO | 2020026217 A1 | 2/2020 | |
| WO | 2020206328 A1 | 10/2020 | |

* cited by examiner

ELECTRO-ANATOMICAL MAPPING AND ANNOTATION PRESENTED IN ELECTROPHYSIOLOGICAL PROCEDURES

FIELD OF THE INVENTION

The present invention relates generally to medical devices, and particularly to methods and systems for improving sensing of unipolar signals in patient heart, and improving accuracy of annotations presented to a user.

BACKGROUND OF THE INVENTION

Various techniques for analyzing and annotating electrophysiological signals have been published.

For example, U.S. Patent Application Publication 2020/0367751 describes a device for detecting points and/or regions of rotational electrophysiological activity in or on a heart. The device comprises an input for receiving spatiotemporal electrophysiological data corresponding to a plurality of spatial locations in or on the heart, a time feature extractor for providing time values indicative of times of occurrence of a predetermined feature of a plurality of electric potential waveforms at the spatial location, a mapping unit for providing pairs of adjacent spatial locations, a directed graph generator for generating a directed graph comprising directed edges, and a topological feature analyzer.

U.S. Patent Application Publication 2018/0303414 describes systems, devices and methods for performing precise treatment, mapping, and/or testing of tissues.

SUMMARY OF THE INVENTION

An embodiment of the present invention that is described herein provides a catheter, including (a) a shaft for insertion into a heart of a patient, (b) an expandable distal-end assembly, which is coupled to the shaft and is configured to make contact with tissue of the heart, (c) at least first and second electrocardiogram (ECG) electrodes, which are coupled to an outer surface of the expandable distal-end assembly, and when placed in contact with the tissue, are configured to sense ECG signals in the tissue, and (d) a reference electrode, which is positioned within an inner volume of the distal-end assembly, and in an expanded position of the distal-end assembly, the reference electrode: (i) has no physical contact with the tissue, and (ii) is positioned at a first distance from the first ECG electrode and at a second distance from the second ECG electrode, and a difference between the first and second distances is smaller than a predefined threshold.

In some embodiments, the expandable distal-end assembly includes at least first and second splines, and the first and second ECG electrodes are coupled to the first and second splines, respectively. In other embodiments, in the expanded position, the reference electrode is positioned at least 9 mm from the tissue. In yet other embodiments, in the expanded position, the predefined threshold is smaller than 1 mm.

In an embodiment, at least one of the ECG signals includes a unipolar ECG signal, which is sensed in the tissue relative to the reference electrode. In another embodiment, the catheter includes a processor, which is configured to calculate, based on the ECG signals sensed at one or more positions on the tissue, one or more respective local activation times (LATs), which are indicative of an electrophysiological wave propagating in the tissue. In yet another embodiment, based on the calculated LATs, the processor is configured to display to a user at least an annotation indicative of a timing error in a rhythm of the heart.

In some embodiments, the processor is configured to display at least the annotation over a graph of at least one of the ECG signals. In other embodiments, the processor is configured to display at least the annotation in a bar graph. In yet other embodiments, the processor is configured to display in the bar graph at least a first annotation indicative of a first type of the timing error, and a second different annotation, which is indicative of a second type of the timing error, different from the first type.

There is additionally provided, in accordance with an embodiment of the present invention, a method including inserting, into a heart of a patient, an expandable distal-end assembly having an expanded position for making contact with tissue of the heart, the distal-end assembly includes: (i) at least first and second electrocardiogram (ECG) electrodes, which are coupled to an outer surface of the distal-end assembly for sensing ECG signals with the tissue when placed in contact with the tissue, and (ii) a reference electrode, which is positioned within an inner volume of the distal-end assembly, and in the expanded position: (a) has no physical contact with the tissue, and (b) is positioned at a first distance from the first ECG electrode and at a second distance from the second ECG electrode, and a difference between the first and second distances is smaller than a predefined threshold. The distal-end assembly is expanded for placing at least the first and second ECG electrodes in contact with the tissue, and ECG signals are sensed in the tissue using at least the first and second ECG electrodes.

The present invention will be more fully understood from the following detailed description of the embodiments thereof, taken together with the drawings in which:

DETAILED DESCRIPTION OF EMBODIMENTS

Overview

Some electrophysiological (EP) procedures require electro-anatomical (EA) mapping of heart tissue using electrodes for acquiring unipolar electrocardiogram (ECG) signals in the tissue in question. The term "unipolar signal" refers to a signal acquired by a sensing electrode, which is placed in contact with the tissue in question, relative to a reference electrode.

In principle, it is possible to measure the ECG signals relative to a reference annotation measured on one or more external reference electrodes positioned on the patient skin using a suitable patch. Moreover, it is possible to calculate, based on the acquired ECG signals, values local activation times (LAT) of an EP wave propagating in the tissue in question. For example, a unipolar signal sensed by a given ECG electrode may constitute the difference between the potential at the given electrode 88 and the Wilson Central Terminal (WCT) set of body surface electrodes positioned on the right arm, left arm, and left leg of the patient. However, using a set of one or more external reference electrode may introduce noise, inaccuracy and/or instability to the sensing of the ECG signals. These inaccuracy and/or instability may result in wrong calculation of the LAT values, and therefore wrong binning and wrong annotations of arrhythmias based on the ECG signals and calculated LAT values.

In some embodiments, a system for improving the sensing of ECG signals comprises a catheter and a processor. The catheter comprises a shaft for insertion into a heart of a patient, an expandable distal-end assembly coupled to the shaft, multiple ECG electrodes, and one or more reference electrodes. In some embodiments, the distal-end assembly is configured to have a collapsed position for being moved to a target location, and an expanded position for making contact with the tissue in question. In the present example the catheter comprises at least first and second ECG electrodes, which are coupled to an outer surface of the expandable distal-end assembly, and, when placed in contact with the tissue, are configured to sense ECG signals in the tissue.

In some embodiments, the catheter comprises a single reference electrode, which is positioned within the inner volume of the distal-end assembly, for example, on a shaft positioned at the center of the distal-end assembly when expanded to the expanded position. Moreover, in the expanded position of the distal-end assembly, the reference electrode has no physical contact with the tissue and in the present example, has a distance of at least 9 mm from the tissue in question. Moreover, the reference electrode is positioned at a first distance from the first ECG electrode and at a second distance from the second ECG electrode. The first and second distances are typically similar, in other words, the difference between the first and second distances is smaller than a predefined threshold, e.g., about 1 mm.

In some embodiments, the processor is configured to receive from the ECG electrodes in contact with the tissue, unipolar ECG signals measured relative to the reference electrode, and to calculate one or more local activation times (LATs), which are indicative of the EP wave propagating in the tissue.

In some embodiments, based on the calculated LATs, the processor is configured to display to a user of the system one or more annotations indicative of respective one or more timing errors in the rhythm of the heart. The processor is further configured to display the one or more annotations over one or more graphs of the unipolar ECG signals. Additionally or alternatively, the processor is configured to display a bar graph having two or more types of timing errors resulting in wrong annotations.

The disclosed techniques improve the quality of unipolar ECG signals sensed in the patient heart, and the accuracy of annotations presented to a user during an electrophysiological procedure. Moreover, the disclosed techniques improve the quality of EA mapping and the success rate of ablation procedures carried out based on the EA mapping.

System Description

Figure 1:
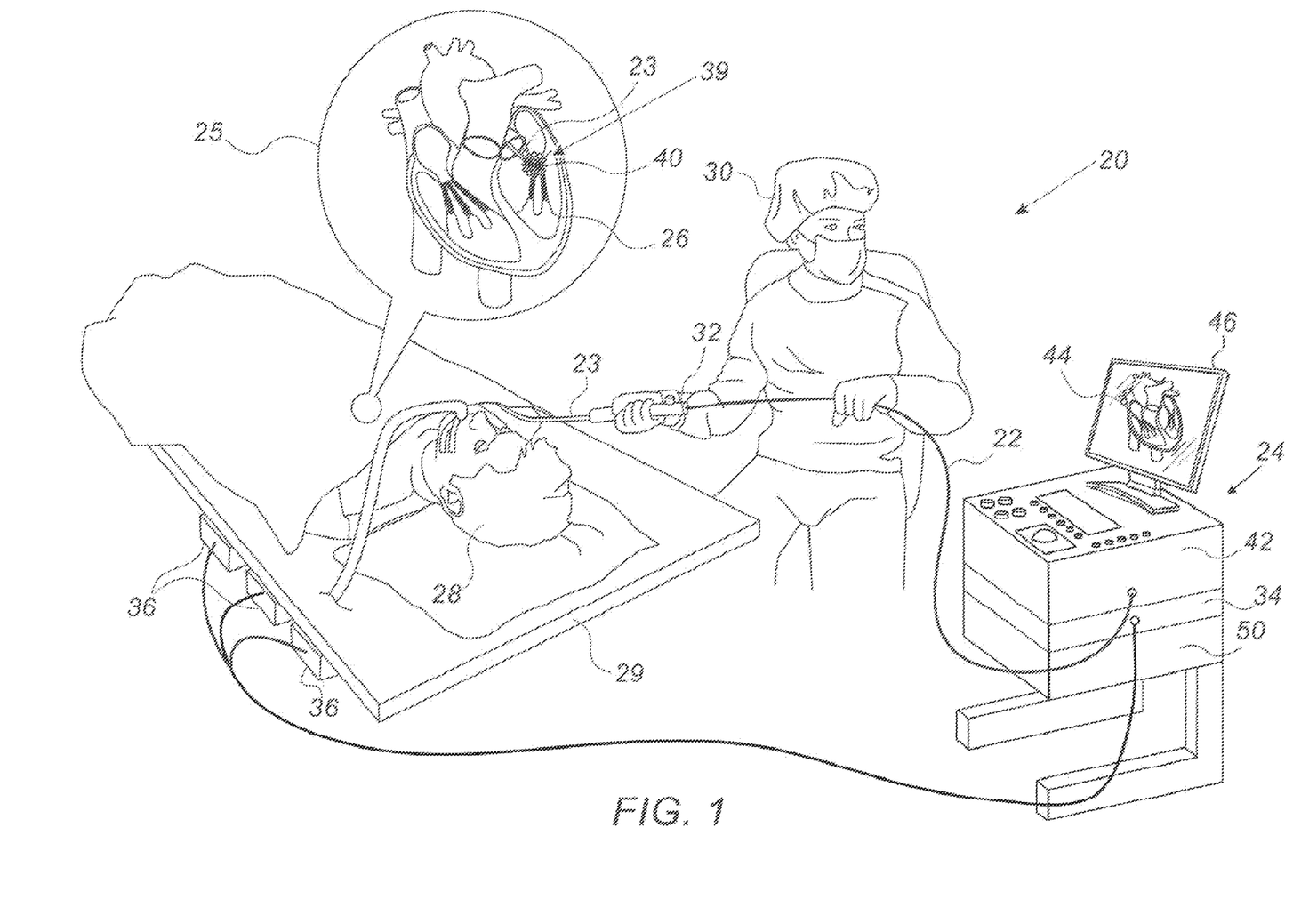
FIG. 1 is a schematic, pictorial illustration of a catheter-based position-tracking and ablation system, in accordance with an embodiment of the present invention.

FIG. 1 is a schematic, pictorial illustration of a catheter-based position-tracking and ablation system 20, in accordance with an embodiment of the present invention. In some embodiments, system 20 comprises a catheter 22, in the present example an expandable cardiac catheter having a basket shape, and a control console 24. In the embodiment described herein, catheter 22 may be used for any suitable therapeutic and/or diagnostic purposes, such as but not limited to electro-anatomical (EA) mapping and/or ablation of tissue in a heart 26.

In some embodiments, console 24 comprises a processor 42, typically a general-purpose computer, with suitable front end and interface circuits for receiving signals from catheter 22 and for controlling other components of system 20 described herein. Processor 42 may be programmed in software to carry out the functions that are used by the system, and is configured to store data for the software in a memory 50. The software may be downloaded to console 24 in electronic form, over a network, for example, or it may be provided on non-transitory tangible media, such as optical, magnetic or electronic memory media. Alternatively, some or all of the functions of processor 42 may be carried out using an application-specific integrated circuit (ASIC) or any suitable type of programmable digital hardware components.

Reference is now made to an inset 25. In some embodiments, catheter 22 comprises a distal-end assembly 40 having multiple splines (shown in detail in FIG. 2 below), and a shaft 23 for inserting distal-end assembly 40 to a target location for ablating tissue in heart 26. During an ablation procedure, physician 30 inserts catheter 22 through the vasculature system of a patient 28 lying on a table 29. Physician 30 moves distal-end assembly 40 to the target location in heart 26 using a manipulator 32 near a proximal end of catheter 22, which is connected to interface circuitry of processor 42.

In some embodiments, catheter 22 comprises one or more position sensor(s) 39 of a position tracking system, which is coupled to the distal end of catheter 22, e.g., in close proximity to distal-end assembly 40. In the present example, position sensors 39 comprise a magnetic position sensor, but in other embodiments, any other suitable type of position sensor (e.g., other than magnetic-based) and corresponding position tracking system may be used.

Reference is now made back to the general view of FIG. 1. In some embodiments, during the navigation of distal-end assembly 40 in heart 26, processor 42 receives signals from magnetic position sensors 39 in response to magnetic fields from external field generators 36, for example, for the purpose of measuring the position of distal-end assembly 40 in heart 26. In some cases distal-end assembly 40 comprises two position sensors, so as to control the level of expansion of distal-end assembly 40. In some embodiments, console 24 comprises a driver circuit 34, which is configured to drive magnetic field generators 36. Magnetic field generators 36 are placed at known positions external to patient 28, e.g., below table 29.

In some embodiments, processor 42 is configured to display, e.g., on a display 46 of console 24, the tracked position of distal-end assembly 40 overlaid on an image 44 of heart 26.

The method of position sensing using external magnetic fields is implemented in various medical applications, for example, in the CARTO™ system, produced by Biosense Webster Inc. (Irvine, Calif.) and is described in detail in U.S. Pat. Nos. 5,391,199, 6,690,963, 6,484,118, 6,239,724, 6,618,612 and 6,332,089, in PCT Patent Publication WO 96/05768, and in U.S. Patent Application Publications 2002/0065455 A1, 2003/0120150 A1 and 2004/0068178 A1, whose disclosures are all incorporated herein by reference.

Distal-End Assembly Having a Central Reference Electrode

Figure 2:
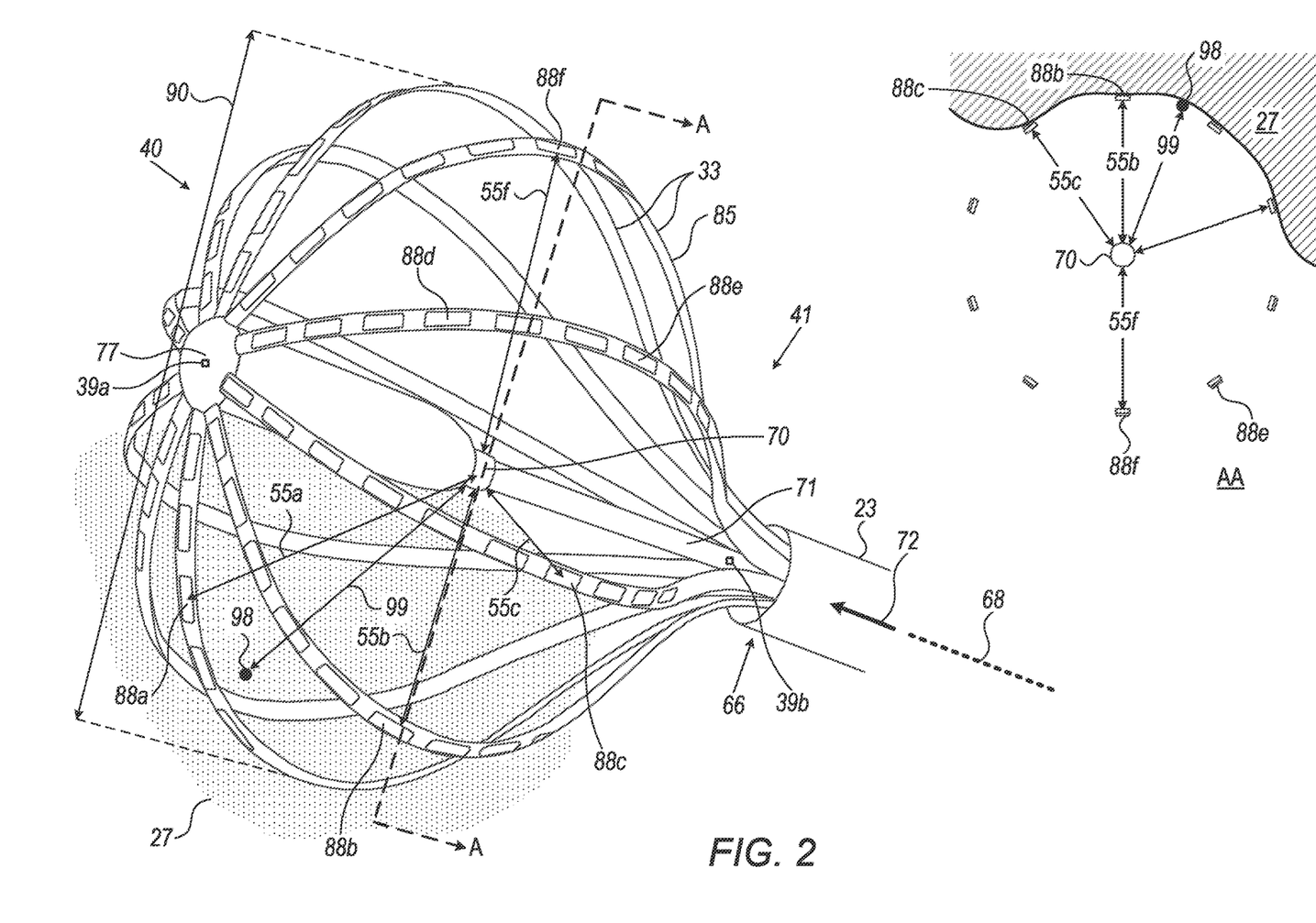
FIG. 2 is a schematic, side view of a distal-end assembly of a catheter, in accordance with an embodiment of the present invention.

FIG. 2 is a schematic, side view of distal-end assembly 40, in accordance with an embodiment of the present invention.

In some embodiments, distal-end assembly 40 is coupled to shaft 23 and is navigated by physician 30 to be placed in contact with tissue in question of heart 26 or with tissue of any other organ of the patient, as described in FIG. 1 above.

In some embodiments, distal-end assembly 40 is expandable, in the present example has a basket shape, but in other embodiments, distal-end assembly 40 may have any other suitable type of an expandable assembly.

In some embodiments, distal-end assembly 40 has splines 33 coupled between a proximal apex 66 and a distal apex 77 of distal-end assembly 40. In the present example, at least one of and typically all splines 33 are made from any suitable biocompatible material, and are electrically isolated from one another, e.g., by apexes 66 and 77 or using any other suitable electrically insulating apparatus.

In some embodiments, at least one of and typically all splines 33 have electrocardiogram (ECG) electrodes, referred to herein as electrodes 88 for brevity. In the present example, each spline 33 has one or more electrodes 88 coupled to an outer surface 85 of the spline. In the context of the present disclosure and in the claims, the term "outer surface" refers to a surface of splines 33 intended to be placed in contact with tissue 27 of heart 26. Electrodes 88 are configured to sense ECG signals in tissue 27. Note that at least one of electrodes 88 is configured to sense electrogram (EGM) signals in tissue 27 of heart 26.

In some embodiments, apexes 66 and 77 are movable relative to one another so as to expand and collapse distal-end assembly 40. For example, apex 66 is moved distally in a direction 72, which is parallel to an axis 68 of catheter 22, so as to expand distal-end assembly 40. Similarly, apex 66 is moved proximally along axis 68 (i.e., opposite to direction 72), so as to collapse distal-end assembly 40. In the present example, axis 68 constitutes a longitudinal axis of both catheter 22 and distal-end assembly 40.

In some embodiments, distal-end assembly 40 may have two position sensors 39a and 39b, which are coupled to, or in adjacent to, apexes 77 and 66, respectively. Based on the position signals received from position sensors 39a and 39b, processor 42 calculates the distance between apexes 66 and 77, and thereby, the expansion-level of distal-end assembly 40.

In some embodiments, distal-end assembly 40 has a reference electrode 70, which is positioned within an inner volume 41 of distal-end assembly 40. In the context of the present disclosure and in the claims, the term "inner volume" refers to the space confined between splines 33. Thus, the larger the expansion-level of distal-end assembly 40, the larger the space confined within inner volume 41.

In some embodiments, reference electrode 70 has no physical contact with tissue 27. In the example of FIG. 2, reference electrode 70 is coupled to a shaft 71, which is extended along axis 68, so that reference electrode 70 is positioned at the center of inner volume 41, and therefore, is also referred to herein as a central electrode.

In some embodiments, when distal-end assembly 40 is placed in contact with tissue 27 of heart 26, one or more splines 33 and electrodes 88 are placed in contact with tissue 27. In such embodiments, reference electrode 70 is positioned at a distance 99 from a point 98, which represents a point on the surface of tissue 27 that is in the closest proximity (from among all the other points on the surface of tissue 27) to reference electrode 70.

In some embodiments, reference electrode 70 is positioned at distances 55a, 55b, 55c and 55f, from electrodes 88a, 88b, 88c and 88f, respectively. In the context of the present disclosure, the term electrode(s) 88 refers to any electrode from among electrodes 88a, 88b, 88c, 88d, 88e, and 88f. When distal-end assembly 40 is fully expanded and has a maximal diameter 90, all distances 55 (e.g., distances 55a, 55b, 55c and 55f) have approximately the same size. For example, the difference between any pair of distances selected from among distances 55a, 55b, 55c and 55f, is smaller than a predefined threshold (e.g., about 1 mm), whereas at the fully expanded position, diameter 90 may have a size between about 18 mm and 30 mm, or any other suitable size. Note that the difference between any pair of distances may also be defined in percentage of maximal diameter 90 when distal-end assembly 40 is in the fully expanded position.

In the context of the present disclosure and in the claims, the terms "about" or "approximately" for any numerical values or ranges indicate a suitable dimensional tolerance that allows the part or collection of components to function for its intended purpose as described herein. Moreover, the terms "about" or "approximately" may also be used for comparing between a physical dimension, or a measurable feature of two or more elements, and the terms "about" or "approximately" may indicate a suitable dimensional tolerance between the compared elements.

Reference is now made to a sectional-view AA of distal-end assembly 40 in the fully expanded position shown in the general view of FIG. 2.

In some embodiments, electrodes 88b and 88c are placed in contact with tissue 27, electrode 55f is not in contact with tissue 27, and distances 55b, 55c and 55f have a similar size. Note that electrode 88a is also placed in contact with tissue 27, but is not in the plane of sectional-view AA, and therefore, is not shown therein. Moreover, distance 99 represents the minimal distance between reference electrode 70 and tissue 27. In the present example, distance 99 is larger than about 9 mm.

In some embodiments, distal-end assembly 40 is designed such that in an expanded position, reference electrode 70 is positioned at a similar distance from all electrodes 88 (e.g., electrodes 88a, 88b, 88c, 88d, 88e, and 88f). The term "similar distance" refers to a difference between distances 55, which is smaller than a predefined threshold, such as the threshold defined above, or any other suitable threshold. More specifically, in the plane shown in sectional-view AA, all the distances between central electrode 70 and electrodes 88 have a similar size (e.g., the difference between the sizes are smaller than the aforementioned threshold). Moreover, central electrode 70 is also located at a predefined minimal distance from tissue 27. In the present example, at a distance larger than about 9 mm, which is represented in sectional-view AA by distance 99.

Reference is now made back to the general view of FIG. 2. In some embodiments, during electro-anatomical mapping of tissue 27 in heart 26, ECG electrodes 88 are configured to sense ECG signals in tissue 27, and processor 42 is configured to estimate, based on the sensed ECG signals, the local activation time (LAT) values of EP waves propagating in heart 26 in close proximity to and also along tissue 26. Processor 42 calculates the LAT values, inter alia, based on the timing of the multiple ECG signals acquired by and received from multiple ECG electrodes 88.

In principle, it is possible to measure the ECG signals and to calculate the LAT values relative to a reference annotation measured on one or more external reference electrodes (not shown) positioned on the skin of patient 28 using a suitable patch. For example, a unipolar signal sensed by a given ECG electrode 88 may constitute the difference between the potential at given electrode 88 and the Wilson Central Terminal (WCT) set of body surface electrodes (not shown) positioned on the right arm, left arm, and left leg of patient 28. However, using a set of one or more external reference electrode may introduce noise, inaccuracy and/or instability to the sensing of the ECG signals. These inaccuracy and/or instability may result in wrong calculation of the LAT values, and therefore wrong binning and wrong annotations of the ECG signals and calculated LAT values.

In some embodiments, the accuracy and stability of the calculated LAT and of the binning and annotation of the ECG signals are improved by sensing the unipolar signals between reference electrode 70 and electrodes 88 placed in contact with tissue 27.

In other embodiments, in addition to or instead of sensing unipolar ECG signals between reference electrode 70 and electrodes 88 placed in contact with tissue 27, reference electrode 70 may be used, for example, as a reference electrode for applying, e.g., to tissue 27, a unipolar ablation signal between one or more ablation electrodes (not shown) of a given spline 33 and reference electrode 70. Note that in such embodiments (i.e., ECG sensing and tissue ablation), reference electrode 70 is not intended to be placed in contact with tissue 27 and the one or more electrodes of given spline 33 are placed in contact with tissue 27.

These particular configurations of system 20 and distal-end assembly 40 are shown by way of example, in order to illustrate certain problems that are addressed by embodiments of the present invention and to demonstrate the application of these embodiments in enhancing the performance of such a system and electrophysiological applications. Embodiments of the present invention, however, are by no means limited to this specific sort of example system or example applications, and the principles described herein may similarly be applied to other sorts of medical system, using any other suitable configuration of distal-end assembly having any suitable arrangement of sensing and/or ablation electrodes, and a reference electrodes that, at least during the procedure, has no physical contact with the tissue in question.

Figure 3:
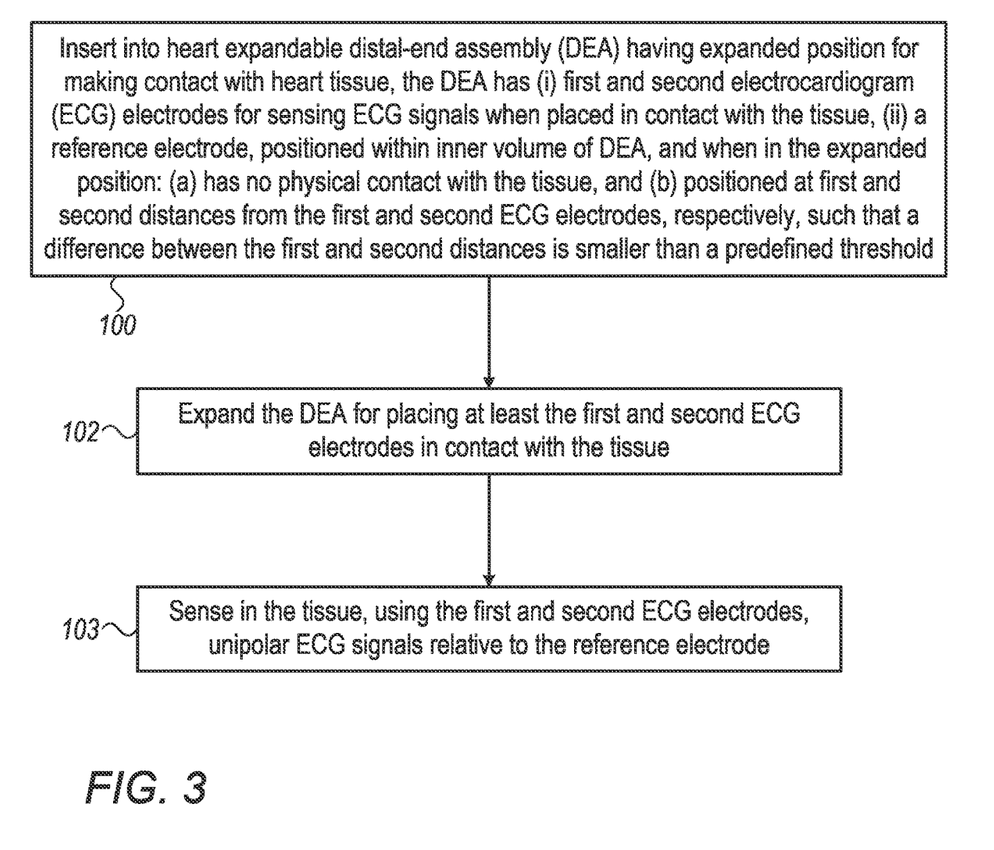
FIG. 3 is a flow chart that schematically illustrates a method for sensing unipolar ECG signals in tissue, in accordance with an embodiment of the present invention.

FIG. 3 is a flow chart that schematically illustrates a method for sensing unipolar ECG signals in tissue 27, in accordance with an embodiment of the present invention.

The method begins at a catheter insertion step 100, with physician 30 inserting distal-end assembly 40 into a cavity of heart 26. Distal-end assembly 40 has: (i) a collapsed position for moving catheter 22 to a target location in tissue 27 of heart 26, and (ii) an expanded position for placing electrodes 88 in contact with tissue 27, or with any other tissue in question. In the example of FIG. 2, at least electrodes 88a, 88b and 88c are placed in contact with tissue 27.

In some embodiments, distal-end assembly 40 comprises reference electrode 70, which is positioned within inner volume 41 of distal-end assembly 40, and in the expanded position of distal-end assembly 40, reference electrode 70 has no physical contact with tissue 27, and typically distance 99 is larger than about 9 mm.

In some embodiments, reference electrode 70 is positioned at distances 55a, 55b, 55c and 55f from electrodes 88a, 88b, 88c and 88f, respectively. The difference between any pair of distances 55a, 55b, 55c and 55f is smaller than a predefined threshold, e.g., about 1 mm. Moreover, when distal-end assembly 40 is expanded (e.g., as shown in FIG. 2 above), reference electrode 70 has no physical contact with tissue 27, and in the present example, reference electrode 70 is positioned at a distance of at least 9 mm from tissue 27.

At an electrode placement step 102, after positioning distal-end assembly 40 in close proximity to tissue 27, physician 30 uses manipulator 32 or any other suitable control knob for expanding distal-end assembly 40 to an expanded position, so that at least electrodes 88a, 88b and 88c are placed in contact with tissue 27, as depicted, for example, in FIG. 2 above.

At a unipolar signal sensing step 103 that concludes the method, processor 42 receives from at least electrodes 88a, 88b and 88c, unipolar ECG signals measured relative to reference electrode 70.

In some embodiments, based on the sensed unipolar ECG signals, processor 42 is configured to calculate one or more local activation times (LATs), which are indicative of the EP wave propagating in tissue 27. Based on the calculated LATs, processor 42 is further configured to display to physician 30 one or more annotations indicative of respective one or more timing errors identified in the rhythm of heart 26. Moreover, processor 42 is configured to display the one or more annotations over one or more graphs of the unipolar ECG signals.

Although the embodiments described herein mainly address electro-anatomical mapping and analysis in electrophysiological applications, the methods and systems described herein can also be used in other applications.

It will thus be appreciated that the embodiments described above are cited by way of example, and that the present invention is not limited to what has been particularly shown and described hereinabove. Rather, the scope of the present invention includes both combinations and sub-combinations of the various features described hereinabove, as well as variations and modifications thereof which would occur to persons skilled in the art upon reading the foregoing description and which are not disclosed in the prior art. Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

The invention claimed is:

1. A catheter system, comprising:
   a shaft for insertion into a heart of a patient;
   an expandable distal-end assembly, which is coupled to the shaft and is configured to make contact with tissue of the heart;
   at least first and second electrocardiogram (ECG) electrodes, which are coupled to an outer surface of the expandable distal-end assembly, and, when placed in contact with the tissue, are configured to sense ECG signals in the tissue;
   a reference electrode, which is positioned within an inner volume of the expandable distal-end assembly, and wherein in an expanded position of the expandable distal-end assembly, the reference electrode: (i) has no physical contact with the tissue, and (ii) is positioned at a first distance from the first ECG electrode and at a second distance from the second ECG electrode, wherein a difference between the first and second distances is smaller than a predefined threshold; and
   a processor configured to:
      calculate, based on the ECG signals sensed at one or more positions on the tissue, one or more respective local activation times (LATs), which are indicative of an electrophysiological wave propagating in the tissue;

identify, based at least in part on the calculated LATs, a timing error of a rhythm of the heart; and output for display an annotation over a graph of at least one of the ECG signals, the annotation being indicative of the timing error identified in the rhythm of the heart.

2. The catheter system according to claim 1, wherein the expandable distal-end assembly comprises at least first and second splines, and wherein the first and second ECG electrodes are coupled to the first and second splines, respectively.

3. The catheter system according to claim 1, wherein in the expanded position, the reference electrode is positioned at least 9 mm from the tissue.

4. The catheter system according to claim 1, wherein at least one of the ECG signals comprises a unipolar ECG signal, which is sensed in the tissue relative to the reference electrode.

5. The catheter system according to claim 1, wherein the processor is configured to display at least the annotation in a bar graph.

6. The catheter system according to claim 5, wherein the processor is configured to display in the bar graph at least a first annotation indicative of a first type of the timing error, and a second different annotation, which is indicative of a second type of the timing error, different from the first type.

7. The catheter system according to claim 1, wherein the reference electrode is disposed on the shaft.

8. The catheter system according to claim 1, wherein the reference electrode is further configured as a reference electrode for applying a unipolar ablation signal between one or more ablation electrodes disposed on the expandable distal-end assembly and the reference electrode.

9. A method, comprising:

inserting, into a heart of a patient, an expandable distal-end assembly having an expanded position for making contact with tissue of the heart, the expandable distal-end assembly comprising: (i) at least first and second electrocardiogram (ECG) electrodes, which are coupled to an outer surface of the expandable distal-end assembly for sensing ECG signals with the tissue when placed in contact with the tissue, and (ii) a reference electrode, which is positioned within an inner volume of the expandable distal-end assembly, and in the expanded position: (a) has no physical contact with the tissue, and (b) is positioned at a first distance from the first ECG electrode and at a second distance from the second ECG electrode, wherein a difference between the first and second distances is smaller than a predefined threshold;

expanding the expandable distal-end assembly for placing at least the first and second ECG electrodes in contact with the tissue;

sensing ECG signals in the tissue using at least the first and second ECG electrodes;

calculating, based on the ECG signals sensed at one or more positions on the tissue, one or more respective local activation times (LATs), which are indicative of an electrophysiological wave propagating in the tissue;

identifying, based at least in part on the calculated LATs, a timing error of a rhythm of the heart; and outputting for display an annotation over a graph of at least one of the ECG signals, the annotation being indicative of the timing error identified in the rhythm of the heart.

10. The method according to claim 9, wherein the expandable distal-end assembly comprises at least first and second splines, and wherein the first and second ECG electrodes are coupled to the first and second splines, respectively.

11. The method according to claim 9, wherein expanding the expandable distal-end assembly comprises positioning the reference electrode at least 9 mm from the tissue.

12. The method according to claim 9, wherein sensing the ECG signals comprises sensing in the tissue a unipolar ECG signal relative to the reference electrode.

13. The method according to claim 9, wherein displaying at least the annotation comprises displaying at least the annotation in a bar graph.

14. The method according to claim 13, wherein displaying at least the annotation in the bar graph comprises displaying in the bar graph, at least a first annotation indicative of a first type of the timing error, and a second different annotation, which is indicative of a second type of the timing error, different from the first type.

* * * * *